US012204589B2

United States Patent
Suzuki et al.

(10) Patent No.: US 12,204,589 B2
(45) Date of Patent: Jan. 21, 2025

(54) INFORMATION PROCESSING SYSTEM, METHOD, PROGRAM AND DATA STRUCTURE

(71) Applicant: SHISEIDO COMPANY, LTD., Tokyo (JP)

(72) Inventors: Ikuhiro Suzuki, Tokyo (JP); Eiko Kondo, Tokyo (JP); Yuko Shiheido, Tokyo (JP); Taizo Fujiyama, Tokyo (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 17/755,166

(22) PCT Filed: Apr. 13, 2020

(86) PCT No.: PCT/JP2020/016328
§ 371 (c)(1),
(2) Date: Apr. 22, 2022

(87) PCT Pub. No.: WO2021/084781
PCT Pub. Date: May 6, 2021

(65) Prior Publication Data
US 2022/0414160 A1    Dec. 29, 2022

(30) Foreign Application Priority Data
Oct. 30, 2019 (JP) ................. 2019-197177

(51) Int. Cl.
*G06F 16/903* (2019.01)
*G06F 16/9032* (2019.01)

(52) U.S. Cl.
CPC .... *G06F 16/90344* (2019.01); *G06F 16/9032* (2019.01); *G06F 2216/11* (2013.01)

(58) Field of Classification Search
CPC .......... G06F 16/90344; G06F 16/9032; G06F 2216/11; G06F 16/36; G06F 16/903;
(Continued)

(56) References Cited

U.S. PATENT DOCUMENTS

2009/0221436 A1* 9/2009 Slanetz ................. G16B 50/20
506/9
2014/0289675 A1   9/2014 Stading et al.
(Continued)

FOREIGN PATENT DOCUMENTS

JP    2005-092794    4/2005
JP    2006-018557    1/2006
(Continued)

OTHER PUBLICATIONS

International Search Report for PCT/JP2020/016328 mailed on Jun. 9, 2020.
(Continued)

*Primary Examiner* — Richard L Bowen
*Assistant Examiner* — Aryan D Toughiry
(74) *Attorney, Agent, or Firm* — IPUSA, PLLC

(57) ABSTRACT

An information processing system facilitates the extraction of a product relating to a patent or to facilitate the extraction of a patent relating to a product. An information processing system includes a database in which a term associated with a raw material recited in a claim of a patent document and a raw material that corresponds to the term are associated with each other, an acquiring unit configured to acquire patent information, and an extracting unit configured to extract a product containing a raw material that corresponds to a term recited in a claim that is identified by the patent information, with reference to the database and a correspondence between a product and a raw material contained in the product, based on whether the raw material that corresponds (Continued)

to the term and the raw material contained in the product match.

17 Claims, 9 Drawing Sheets

(58) Field of Classification Search
CPC .... G06F 16/284; G06F 16/332; G06F 16/901; G06Q 10/10; G06Q 50/184; G06Q 50/18
See application file for complete search history.

(56) References Cited

U.S. PATENT DOCUMENTS

| | | | | |
|---|---|---|---|---|
| 2015/0278349 | A1* | 10/2015 | Speier | G06Q 10/10 707/722 |
| 2016/0350886 | A1* | 12/2016 | Jessen | G06Q 50/184 |
| 2020/0133946 | A1* | 4/2020 | Kim | G06F 40/30 |

FOREIGN PATENT DOCUMENTS

| | | |
|---|---|---|
| JP | 2015-072573 | 4/2015 |
| WO | 2006/071876 | 7/2006 |

OTHER PUBLICATIONS

"Patent Information Platforms" [online], [Searched on Sep. 20, 2019], Internet<URL: https://www.j-platpat.inpit.go.jp/>.
Notice of Grounds for Revocation with respect to JP Patent No. 6694104, mailed on Feb. 5, 2021.
Cosmetic-Info.jp, a cosmetic raw material search tool Catalog, Aug. 30, 2016.
Extended European Search Report issued in the counterpart European Patent Application No. 20882636.2, mailed Oct. 5, 2023.

* cited by examiner

FIG.3

PATENT NUMBER○○○○○: CLAIM 1

| ELEMENT A | RAW MATERIAL THAT CORRESPONDS TO ELEMENT A | | | BLENDING AMOUNT |
|---|---|---|---|---|
| | INCI | MID | CAS | |
| SILICONE OIL | Dimethicone | 840 | 63148-62-9 | 20~50% |
| | Diphenyl Dimethicone | 3983 | 68083-14-7 | |
| | Phenyl Trimethicone | 2294 | 2116-84-9 | |
| | Cyclomethicone | 637 | 69430-24-6 | |
| | ... | ... | ... | |
| ELEMENT B | RAW MATERIAL THAT CORRESPONDS TO ELEMENT B | | | BLENDING AMOUNT |
| | INCI | MID | CAS | |
| UV ABSORBER | Octocrylene | 1768 | 6197-30-4 | ... |
| | Ethylhexyl Methoxycinnamate | 1792 | 5466-77-3 | |
| | ... | ... | ... | |
| ELEMENT C | RAW MATERIAL THAT CORRESPONDS TO ELEMENT C | | | BLENDING AMOUNT |
| | INCI | MID | CAS | |
| UV SCATTERER | Talc | 3119 | 14807-96-6 | ... |
| | Titanium Dioxide | 6902 | 13463-67-7 | |
| | ... | ... | ... | |
| ELEMENT D | RAW MATERIAL THAT CORRESPONDS TO ELEMENT D | | | BLENDING AMOUNT |
| | INCI | MID | CAS | |
| ... | ... | ... | ... | ... |
| | ... | ... | ... | |
| | ... | ... | ... | |

| ITEM CLASSIFICATION |
|---|
| SUN CARE |
| SKINCARE |
| ... |
| CONTAINER |
| TUBE |
| JAR |
| ... |
| TARGET PORTION |
| SKIN |
| ... |
| EMULSIFIED TYPE |
| W/O |
| ... |
| DOSAGE FORM |
| CREAM |
| GEL |
| ... |
| VISCOSITY |
| ... |
| pH |
| ... |

FIG.4

| PRODUCT NAME: ○○○○○ | | |
|---|---|---|
| RAW MATERIAL | | |
| INCI | MID | CAS |
| Dimethicone | 840 | 63148-62-9 |
| Aqua | 3342 | 7732-18-5 |
| Alcohol | 65 | 64-17-5 |
| Isododecane | 5088 | 31807-55-3 |
| Ethylhexyl Methoxycinnamate | 1792 | 5466-77-3 |
| Isopropyl Myristate | 1343 | 110-27-0 |
| Polymethyl Methacrylate | 5111 | 9011-14-7 |
| Talc | 3119 | 14807-96-6 |
| Polymethylsilsesquioxane | 7410 | 68554-70-1 |
| Octocrylene | 1768 | 6197-30-4 |
| Dextrin Palmitate | 5210 | 83271-10-7 |
| ... | ... | ... |
| ... | ... | ... |
| ... | ... | ... |
| ... | ... | ... |
| ... | ... | ... |
| ... | ... | ... |
| ITEM CLASSIFICATION | | |
| SUN CARE | | |
| CONTAINER | | |
| TUBE | | |
| TARGET PORTION | | |
| SKIN | | |
| EMULSIFIED TYPE | | |
| W/O | | |
| DOSAGE FORM | | |
| GEL | | |
| VISCOSITY | | |
| 2000mPa·s | | |
| pH | | |
| 7 | | |

FIG.5

| PATENT NUMBER○○○○○: CLAIM 1 | | | |
|---|---|---|---|
| ELEMENT A | RAW MATERIAL THAT CORRESPONDS TO ELEMENT A | | BLENDING AMOUNT |
| | INCI | MID / CAS | |
| SILICONE OIL | Dimethicone | 840 / 63148-62-9 | 20~50% |
| | Diphenyl Dimethicone | 3983 / 68083-14-7 | |
| | Phenyl Trimethicone | 2294 / 2116-84-9 | |
| | Cyclomethicone | 637 / 69430-24-6 | |
| | ... | ... | ... |
| ELEMENT B | RAW MATERIAL THAT CORRESPONDS TO ELEMENT B | | BLENDING AMOUNT |
| | INCI | MID / CAS | |
| UV ABSORBER | Octocrylene | 1768 / 6197-30-4 | ... |
| | Ethylhexyl Methoxycinnamate | 1792 / 5466-77-3 | |
| | ... | ... | |
| ELEMENT C | RAW MATERIAL THAT CORRESPONDS TO ELEMENT C | | BLENDING AMOUNT |
| | INCI | MID / CAS | |
| UV SCATTERER | Talc | 3119 / 14807-96-6 | ... |
| | Titanium Dioxide | 6902 / 13463-67-7 | |
| | ... | ... | |
| ELEMENT D | RAW MATERIAL THAT CORRESPONDS TO ELEMENT D | | BLENDING AMOUNT |
| | INCI | MID / CAS | |
| | ... | ... | ... |
| ... | | | |
| ITEM CLASSIFICATION | SUN CARE | | |
| | SKINCARE | | |
| | ... | | |
| CONTAINER | TUBE | | |
| | JAR | | |
| | ... | | |
| TARGET PORTION | SKIN | | |
| | ... | | |
| EMULSIFIED TYPE | W/O | | |
| | ... | | |
| DOSAGE FORM | CREAM | | |
| | GEL | | |
| | ... | | |
| VISCOSITY | ... | | |
| pH | ... | | |

| PRODUCT NAME: ○○○○○ | | |
|---|---|---|
| RAW MATERIAL | | |
| INCI | MID | CAS |
| Dimethicone | 840 | 63148-62-9 |
| Aqua | 3342 | 7732-18-5 |
| Alcohol | 65 | 64-17-5 |
| Isododecane | 5088 | 31807-55-3 |
| Ethylhexyl Methoxycinnamate | 1792 | 5466-77-3 |
| Isopropyl Myristate | 1343 | 110-27-0 |
| Polymethyl Methacrylate | 5111 | 9011-14-7 |
| Talc | 3119 | 14807-96-6 |
| Polymethylsilsesquioxane | 7410 | 68554-70-1 |
| Octocrylene | 1768 | 6197-30-4 |
| Dextrin Palmitate | 5210 | 83271-10-7 |
| ... | ... | ... |
| ... | ... | ... |
| ... | ... | ... |
| ITEM CLASSIFICATION: SUN CARE | | |
| CONTAINER: TUBE | | |
| TARGET PORTION: SKIN | | |
| EMULSIFIED TYPE: W/O | | |
| DOSAGE FORM: GEL | | |
| VISCOSITY: 2000mPa·s | | |
| pH: 7 | | |

INFORMATION PROCESSING SYSTEM, METHOD, PROGRAM AND DATA STRUCTURE

TECHNICAL FIELD

The present invention relates to an information processing system, method, program, and data structure.

BACKGROUND ART

Conventionally, various searches relating to patents of others or one's own have been carried out. For example, companies are conducting clearance searches to search whether new products infringe on the patent rights of others. Further, searches are being conducted to see whether a product that infringes on their patents are on the market.

In such searches relating to patents, for example, the patent information platform of the Japan Patent Office (Non-Patent Document 1), ingredient labeling described in products, and the like are used.

RELATED-ART DOCUMENTS

Patent Documents

Non-Patent Document 1: "Patent Information Platforms" [online], [Searched on Sep. 20, 2019], Internet <URL: https://www.j-platpat.inpit.go.jp/>

SUMMARY OF THE INVENTION

Problem to be Solved by the Invention

However, in the claims of a patent document, the name of the raw material of the product may not be described as it is, but a superordinate term or an equivalent term may be described. Therefore, it is difficult for a person searching for a patent for a product containing an identified raw material to extract the relevant patent document even if the name of the raw material of the product is searched as a keyword. Further, because the term recited in the claims of the patent document and the name of the raw material of the product are different, it may be difficult to match a potentially infringing product with a patent right.

In consideration of the above, an object of an embodiment of the present invention is to facilitate extraction of a product relating to a patent or facilitating extraction of a patent relating to a product.

Means to Solve the Problem

An aspect of the present invention includes a database in which terms associated with raw materials recited in claims of patent documents and raw materials that correspond to the terms are associated with each other, an acquiring unit configured to acquire patent information, and an extracting unit configured to extract products containing raw materials that correspond to terms recited in claims that are identified by the patent information, with reference to the database and a correspondence between a product and a raw material contained in the product, based on whether the raw material that corresponds to the term and the raw material contained in the product match.

Effects of the Invention

According to the present invention, extraction of a product relating to a patent can be facilitated or extraction of a patent relating to a product can be facilitated.

BRIEF DESCRIPTION OF THE DRAWINGS

FIG. 3 is an example of a patent database according to an embodiment of the present invention;

FIG. 4 is an example of a product database according to an embodiment of the present invention;

FIG. 5 is a diagram for explaining calculation of a matching rate between information in the patent database and information in the product database according to an embodiment of the present invention;

MODE FOR CARRYING OUT THE INVENTION

Hereinafter, embodiments of the present invention will be described with reference to the drawings.

In the present disclosure, a case of extracting a cosmetic relating to a patent or a case of extracting a patent relating to a cosmetic will be mainly described as an example, but the present invention can be applied to any product, and is not limited to cosmetics.

Figure 1:
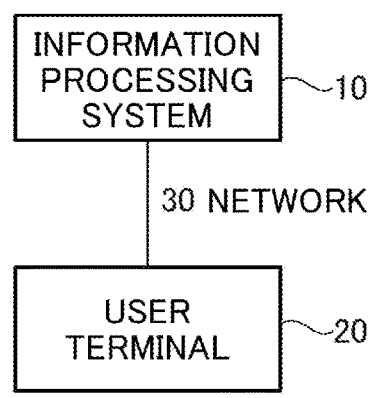
FIG. 1 is a diagram of an overall configuration according to an embodiment of the present invention.

FIG. 1 is a diagram of an overall configuration according to an embodiment of the present invention. As illustrated in FIG. 1, an information processing system 10 is communicatively connected to one or more user terminals 20 via any network 30. Each of them will be described below.

The information processing system 10 may extract a product relating to a patent according to a request from the user terminal 20. The information processing system 10 may extract a patent relating to the product according to a request from the user terminal 20. The information processing system 10 includes one or more computers. Further, the information processing system 10 can transmit and receive data from the user terminal 20 via any network 30. Hereinafter, the information processing system 10 will be described in detail with reference to FIG. 2.

The user terminal 20 is a terminal used by a person who desires to extract a patent relating to a product or a person who desires to extract a patent relating to a product. Specifically, the user terminal 20 transmits a request input into the user terminal 20 to the information processing system 10. The user terminal 20 receives a result extracted in response to the request from the user terminal 20 (i.e., product information or patent information) from the information processing system 10 and displays the result on a display. The user terminal 20 may be any terminal, such as a personal computer, a tablet terminal, a smartphone, or the like.

Figure 2:
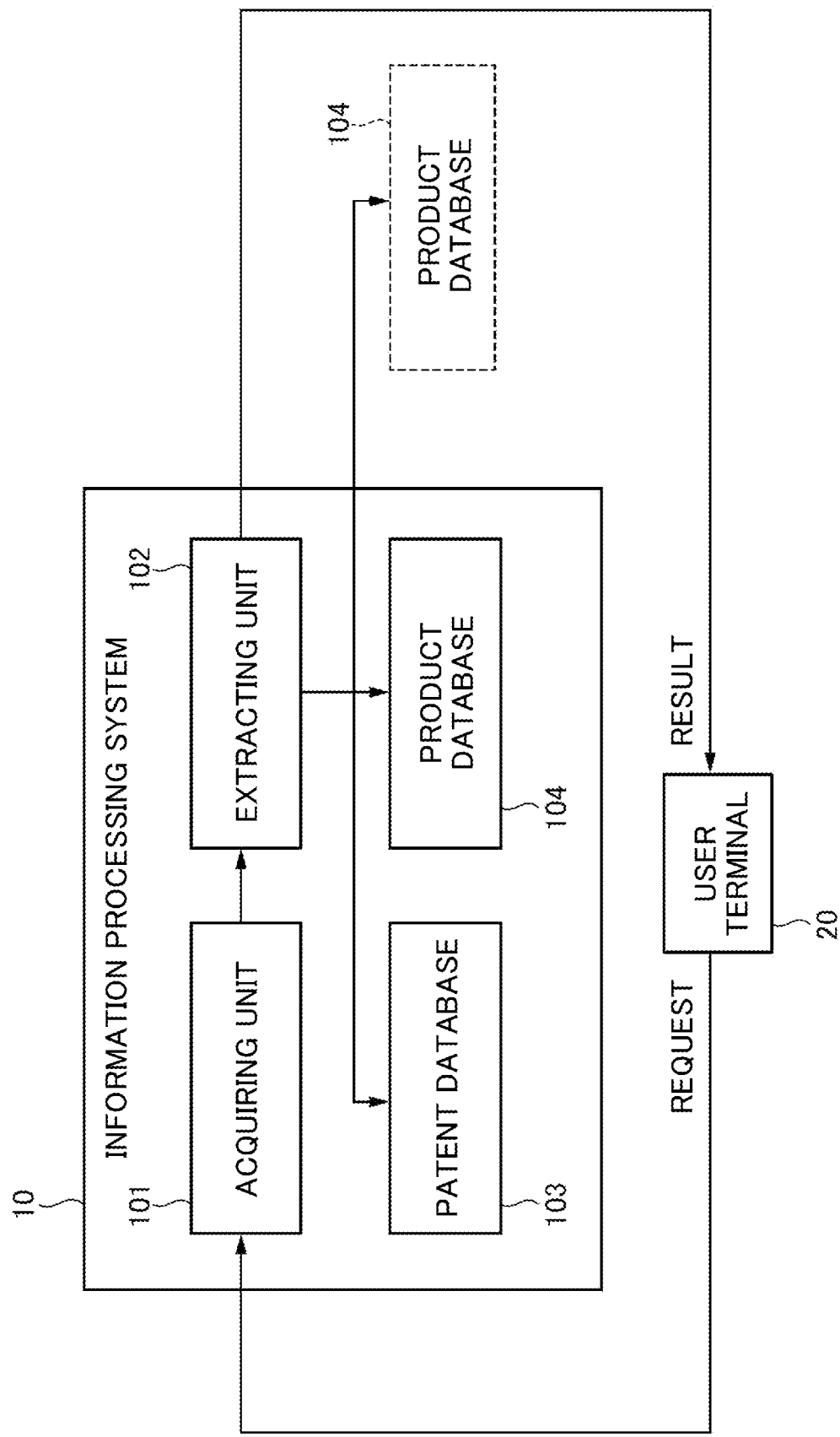
FIG. 2 is a functional block diagram of an information processing system according to an embodiment of the present invention.

FIG. 2 is a functional block diagram of the information processing system 10 according to the embodiment of the present invention. As illustrated in FIG. 2, the information processing system 10 may include an acquiring unit 101, an extracting unit 102, a patent database 103, and a product database 104. Further, the information processing system 10 can function as the acquiring unit 101 and the extracting unit 102 by executing a program.

The information processing system 10 may refer to a product database 104 inside the information processing system 10 or may refer to a product database 104 outside the information processing system 10.

The acquiring unit 101 receives data of the request input into the user terminal 20 from the user terminal 20. Hereinafter, the description is divided into <Extracting Product Relating to Patent>, <Extracting Patent Relating to Product>, and <Extracting Patent Relating to Formulation>.

<Extracting Product Relating to Patent>

The acquiring unit 101 acquires patent information from the user terminal 20. The patent information is information that identifies a patent right or a patent application. For example, the patent information may be a patent number (registration number), a patent application number, a publication number, a patent appeal number, or the like.

<Extracting Patent Relating to Product>

The acquiring unit 101 acquires product information from the user terminal 20. The product information is information that identifies a product. For example, the product information is the name of the product or the like.

<Extracting Patent Relating to Formulation>

In an embodiment of the present invention, a patent relating to a formulation as well as the product may be extracted. The acquiring unit 101 acquires the formulation from the user terminal 20. The formulation includes information indicating the raw materials required to make substances, such as cosmetics. Note that the formulation may also include information on the "blending amount" indicating the amount of the raw material (for example, the ratio of the amount of the raw material to the total amount of the substances, such as cosmetics (for example, in weight, volume, moles, or the like)). The formulation may also include information on "item classification" indicating the category to which the substance such as cosmetics belongs, a "container" indicating a container in which the substance is stored, a "target portion" indicating the body portion to which the substances is applied, an "emulsified type" indicating the emulsified state of the substance, a "dosage form" indicating the form of the substance, a "viscosity" indicating the degree of stickiness of the substance, and "pH" indicating the hydrogen ion index of the substance.

The extracting unit 102 extracts a product based on the patent information acquired by the acquiring unit 101 or extracts a patent based on the product information or the formulation acquired by the acquiring unit 101. Before describing the extracting unit 102 in detail, the patent database 103 and the product database 104 will be described.

The patent database 103 is a database in which terms recited in patent claims of the patent document that are associated with a raw material and raw materials are associated with the corresponding terms. For example, the patent document may be a patent publication, a patent application publication, an international patent application publication, or the like. The patent document also includes procedural amendments. Hereinafter, the patent database 103 will be described in detail with reference to FIG. 3.

FIG. 3 is an example of the patent database 103 according to the embodiment of the present invention. As illustrated in FIG. 3, in the patent database 103, for each claim, a "term (also referred to as an element) associated with a raw material" is associated with a "raw material that corresponds to the term". For example, information of the "element", the "raw material (for example, International Nomenclature of Cosmetic Ingredients (INCI), Monograph ID (MID), Chemical Abstracts Service (CAS), or the like) that corresponds to the element", and a "blending amount" may be stored in association with each other. Further, information such as an "item classification", a "container", a "target portion", an "emulsified type", a "dosage form", a "viscosity", and "pH" may be stored. Each of them will be described below.

The "element (i.e., the term associated with the raw material)" is a component necessary for identifying the claimed invention. The claimed inventions may be an invention of a product, an invention of a method (also referred to as a simple method), or an invention of producing a product. Note that each claim includes one or more "elements".

The "raw material that corresponds to the element" is information for identifying the raw material that corresponds to the "element (i.e., the term associated with the raw material)". For example, the "raw material that corresponds to the element" is an INCI name, a MID, a Chemical Abstracts Service registry number (CAS Registry Number) (registered trademark), or the like. Note that each "element" corresponds to one or more "raw materials that correspond to the element". Each "element" may include one type of information (for example, INCI only) for identifying the raw material that corresponds to the element, or multiple types of information (for example, INCI, MID, and CAS) for identifying the raw material that corresponds to the element.

Here, the relationship between the "element" and the "raw material that corresponds to the element" will be described. As described above, each claim includes one or more "elements". Further, each "element" is associated with one or more of the "raw material that corresponds to the element". For example, the "raw material that corresponds to the element" may be stored based on the contents described in the specification or the like.

The "blending amount" refers to an amount of "element" (i.e., the term associated with the raw material). For example, the "blending amount" is a ratio of the total amount (for example, in weight, volume, moles, or the like) of a product according to the claimed invention (or a product used in a method according to the claimed invention or a product produced by the method according to the claimed invention) with respect to the amount of the "element (i.e., the term associated with the raw material)". For example, information of the "blending amount" may be stored based on the contents described in the specification or the like.

The "item classification" refers to a category to which a product according to the claimed invention (or a product used in a method according to the claimed invention or a product produced by the method according to the claimed invention) belongs (for example, a category classified by the purpose of use of the product). For example, the "item classification" includes sun care, skincare, or the like. For example, information of the "item classification" may be stored based on the contents described in the specification or the like.

The "container" refers to a container containing a product according to the claimed invention (or a product used in a method according to the claimed invention or a product produced by the method according to the claimed invention). For example, the "container" is a tube, a jar, or the like. For example, information of the "container" may be stored based on the contents described in the specification or the like.

The "target portion" refers to a body portion to which a substance according to the claimed invention (or a substance used in a process according to the invention or a substance produced by a process according to the invention) is applied. For example, the "target portion" includes skin, hair, lips, or the like. For example, information of the "target portion" may be stored based on the contents described in the specification or the like.

The "emulsified type" refers to an emulsified state of a product according to the claimed invention (or a product used in a method according to the claimed invention or a product produced by the method according to the claimed invention). For example, the "emulsified type" includes Water in Oil (W/O), Oil in Water (O/W), water, oil, and the like. For example, information of the "emulsified type" may be stored based on the contents described in the specification or the like.

The "dosage form" refers to a form of a product according to the claimed invention (or a product used in a method according to the claimed invention or a product produced by the method according to the claimed invention). For example, the "dosage form" may be a cream, gel, solid, lotion, or the like. For example, information of the "dosage form" may be stored based on the contents described in the specification or the like.

The "viscosity" refers to a degree of stickiness of a product according to the claimed invention (or a product used in a method according to the claimed invention or a product produced by the method according to the claimed invention). For example, information of "viscosity" may be stored based on the contents described in the specification or the like.

The "pH" refers to the hydrogen ion index of a product according to the claimed invention (or a product used in a method according to the claimed invention or a product produced by the method according to the claimed invention). For example, information of the "pH" based on the contents described in the specification or the like is stored.

The description will return to FIG. 2. The product database 104 is a database in which the product and the raw material contained in the product are associated. The product may be any product, not limited to cosmetics. Hereinafter, the product database 104 will be described in detail with reference to FIG. 4.

FIG. 4 is an example of the product database 104 according to the embodiment of the present invention. As illustrated in FIG. 4, in the product database 104, information of the "raw material (for example, INCI, MID, CAS, or the like)" contained in the product is stored for each product. Further, the information such as an "item classification", a "container", a "target portion", an "emulsified type", a "dosage form", a "viscosity", and "pH" may be stored. Each of them will be described below.

The "Raw material" is the information used to identify the raw material contained in the product. For example, the "raw material" is an INCI name, a MID, a CAS registry number (registered trademark), or the like. Each product includes one or more raw materials. Further, each product may also include one type of information (for example, INCI only) for identifying the raw material, or multiple types of information (for example, INCI, MID, and CAS) for identifying the raw material.

The "item classification" refers to a category to which a product belongs (for example, a category classified by the purpose of use of the product). For example, the "item classification" includes sun care, skincare, or the like.

The "container" refers to a container containing a product. For example, the "container" is a tube, a jar, or the like.

The "target portion" refers to a body portion to which a product is applied. For example, the "target portion" includes skin, hair, lips, or the like.

The "emulsified type" refers to an emulsified state of a product. For example, the "emulsified type" includes Water in Oil (W/O), Oil in Water (O/W), water, oil, and the like.

The "dosage form" refers to a form of a product. For example, the "dosage form" may be a cream, gel, solid, lotion, or the like.

The "viscosity" refers to the degree of stickiness of a product.

The "pH" refers to the hydrogen ion index of a product.

In the product database 104, information on the "raw material" contained in the product and the "blending amount" of the raw material may be stored in association with each other. The "blending amount" refers to the amount of the "raw material". For example, "blending amount" is a ratio of the amount of the "raw material" to the total amount of the product (for example, in weight, volume, moles, or the like).

The description will return to the description of the extracting unit 102 in FIG. 2. Hereinafter, the description is divided into <Extracting Product Relating to Patent>, <Extracting Patent Relating to Product>, and <Extracting Patent Relating to Formulation>.

<Extracting Product Relating to Patent>

The extracting unit 102 extracts a product containing a raw material that corresponds to a term recited in the claim to be identified by patent information acquired by the acquiring unit 101.

<<Identify Claim>>

Specifically, the extracting unit 102 identifies a claim based on the patent information acquired by the acquiring unit 101. For example, if a patent publication exists, the extracting unit 102 identifies a claim (for example, claim 1) recited in the patent publication. Further, for example, if a patent publication does not exist, the extracting unit 102 identifies a claim (for example, claim 1) recited in the patent application publication or the international patent application publication. Further, for example, if a patent publication does not exist and a procedural amendment is submitted, the extracting unit 102 identifies a claim (for example, claim 1) recited in the last submitted procedural amendment.

<<Identify Element>>

The extracting unit 102 identifies all the elements recited in the claim to be identified by the patent information with reference to the patent database 103.

<Identify Raw Material that Corresponds to Element>

The extracting unit 102 identifies all the raw materials that correspond to each of the identified elements with reference to the patent database 103. The extracting unit 102 may be configured to identify the "blending amount" of each of the identified elements with reference to the patent database 103. Further, the extracting unit 102 may also be configured to identify at least one of the "item classification", "container", "target portion", "emulsified type", "dosage form", "viscosity", and "pH" of the claim to be identified by the patent information with reference to the patent database 103.

<<Calculate Matching Rate>>

The extracting unit 102 calculates a matching rate between the raw material that corresponds to the element recited in the claim to be identified by the patent information and the raw material contained in the product. Hereinafter, the calculation of the matching rate will be described in detail with reference to FIG. 5.

FIG. 5 is a diagram illustrating the calculation of the matching rate between the information in the patent database 103 and the information in the product database 104 according to the embodiment of the present invention. With reference to the product database 104, the extracting unit 102 determines, for each element, whether at least one of the raw materials that correspond to the elements is contained in the product (i.e., whether the raw materials that correspond to the elements and the raw materials contained in the product match). For example, in FIG. 5, the extracting unit 102 determines that a raw material that corresponds to Element A is contained (i.e., matches) in the product, a raw material that corresponds to Element B is contained (i.e., matches) matches) in the product, a raw material that corresponds to Element C is contained (i.e., matches) in the product, and a raw material that corresponds to Element D is not contained (i.e., does not match) in the product.

The extracting unit 102 may be configured to determine whether the "blending amount" of the element and the "blending amount" of the raw material contained in the product match.

The extracting unit 102 may be configured to determine whether at least one of the "item classification", "container", "target portion", "emulsified type", "dosage form", "viscosity", and "pH" of the claim and at least one of the "item classification", "container", "target portion", "emulsified type", "dosage form", "viscosity", and "pH" of the product match.

The extracting unit 102 calculates a ratio of the "matching number" to "the number of times of determination of matching" as the matching rate. Specifically, the extracting unit 102 calculates the ratio of "the number of elements matching the raw materials of the product" to "the number of all elements". Further, the extracting unit 102 may be configured to calculate the ratio of "the number of elements matching the raw materials and blending amount of the product" to "the number of all elements". Further, the extracting unit 102 may be configured to calculate a matching rate including whether at least one of the "item classification", "container", "target portion", "emulsified type", "dosage form", "viscosity", and "pH" match. A matching rate may be calculated by weighting each of the "elements", "blending amount", "item classification", "container", "application destination", "emulsification form", "dosage form", "viscosity" and "pH" (for example, when the "element" matches, the matching rate is calculated such that the matching rate is higher than when the other items match).

<<Sort>>

The extracting unit 102 lists products in order of a high matching rate or a low matching rate based on the calculated matching rate.

<<Output of Result>>

The extracting unit 102 transmits information of certain products (for example, a predetermined number of products having a high matching rate order) among the listed products to the user terminal 20. For example, the extracting unit 102 transmits information for identifying the product such as the name of the product to the user terminal 20.

The extracting unit 102 may be configured to transmit information of a product in which the matching rate is 100% (i.e., a product is likely to be within the technical scope of the patented invention) to the user terminal 20.

<Extracting Patent Relating to Product>

The extracting unit 102 extracts a claim in which a term associated with a raw material contained in a product to be identified by the product information acquired by the acquiring unit 101 is described.

<<Identify Raw Material>>

Specifically, the extracting unit 102 identifies the raw material contained in the product to be identified by the product information with reference to the product database 104. The extracting unit 102 may be configured to identify the "blending amount" of the identified raw material with reference to the product database 104. Further, the extracting unit 102 may be configured to identify at least one of the "item classification", "container", "target portion", "emulsified type", "dosage form", "viscosity", and "pH" of the product to be identified by the product information with reference to the product database 104.

<<Calculate Matching Rate>>

The extracting unit 102 calculates a matching rate between the raw material contained in the product to be identified by the product information and the raw material that corresponds to the element recited in the claim.

With reference to the patent database 103, the extracting unit 102 determines, for each element of each claim, whether at least one of the raw materials that correspond to the elements is contained in the product (i.e., whether the raw material contained in the product and the raw material that corresponds to the element match).

The extracting unit 102 may be configured to determine whether the "blending amount" of the raw material contained in the product and the "blending amount" of the element match.

The extracting unit 102 may be configured to determine whether at least one of the "item classification", "container", "target portion", "emulsified type", "dosage form", "viscosity", and "pH" of the product and at least one of the "item classification", "container", "target portion", "emulsified type", "dosage form", "viscosity", and "pH" of the claim match.

The extracting unit 102 calculates a ratio of the "matching number" to "the number of times of determination of matching" as the matching rate. Specifically, the extracting unit 102 calculates the ratio of "the number of elements matching the raw materials of the product" to "the number of all elements". Further, the extracting unit 102 may be configured to calculate the ratio of "the number of elements matching the raw materials and blending amount of the product" to "the number of all elements". Further, the extracting unit 102 may be configured to calculate a matching rate including whether at least one of the "item classification", "container", "target portion", "emulsified type", "dosage form", "viscosity", and "pH" match. A matching rate may be calculated by weighting each of the "elements", "blending amount", "item classification", "container", "application destination", "emulsification form", "dosage form", "viscosity" and "pH" (for example, when the "element" matches, the matching rate is calculated such that the matching rate is higher than when the other items match).

<<Sort>>

The extracting unit 102 lists claims (i.e., all claims of all patent documents) in order of a high matching rate or a low matching rate based on the calculated matching rate.

Further, the extracting unit 102 may be configured to list claims 1 (i.e., the claim having the broadest patent right) of each of the patent documents in order of a high matching rate or a low matching rate.

<<Output of Result>>

The extracting unit 102 transmits information of certain claims (for example, a predetermined number of claims having a high matching rate order) among the listed claims to the user terminal 20. For example, the extracting unit 102 transmits information for identifying a claim, such as a patent number and a claim number, to the user terminal 20.

The extracting unit 102 may be configured to transmit information of a certain portion of claims 1's (for example, a predetermined number of claims 1's having a high matching rate order) among the listed claims 1's to the user terminal 20. For example, the extracting unit 102 transmits information (a patent number or the like) for identifying a patent document recited in claim 1 to the user terminal 20.

<Extracting Patent Relating to Formulation>

The extracting unit 102 extracts a claim in which a term associated with a raw material contained in the formulation acquired by the acquiring unit 101 is described.

<<Identify Raw Material>>

Specifically, the extracting unit 102 identifies the raw material contained in the formulation. The extracting unit 102 may be configured to identify the "blending amount" of the raw material contained in the formulation. Further, the extracting unit 102 may be configured to identify at least one of the "item classification", "container", "target portion", "emulsified type", "dosage form", "viscosity", and "pH" included in the formulation.

<<Calculate Matching Rate>>

The extracting unit 102 calculates a matching rate between the raw material contained in the formulation and the raw material that corresponds to the element recited in the claim.

With reference to the patent database 103, the extracting unit 102 determines, for each element of each claim, whether at least one of the raw materials that correspond to the elements is contained in the formulation (i.e., whether the raw material contained in the formulation and the raw material that corresponds to the element match).

The extracting unit 102 may be configured to determine whether the "blending amount" of the raw material contained in the formulation and the "blending amount" of the element match.

The extracting unit 102 may be configured to determine whether at least one of the "item classification", "container", "target portion", "emulsified type", "dosage form", "viscosity", and "pH" of the formulation and at least one of the "item classification", "container", "target portion", "emulsified type", "dosage form", "viscosity", and "pH" of the claim match.

The extracting unit 102 calculates a ratio of the "matching number" to the number of times of determination of matching" as the matching rate. Specifically, the extracting unit 102 calculates the ratio of "the number of elements matching the raw materials of the formulation" to "the number of all elements". Further, the extracting unit 102 may be configured to calculate the ratio of "the number of elements matching the raw materials and blending amount of the formulation" to "the number of all elements". Further, the extracting unit 102 may be configured to calculate a matching rate including whether at least one of the "item classification", "container", "target portion", "emulsified type", "dosage form", "viscosity", and "pH" match. A matching rate may be calculated by weighting each of the "elements", "blending amount", "item classification", "container", "application destination", "emulsification form", "dosage form", "viscosity" and "pH" (for example, when the "element" matches, the matching rate is calculated such that the matching rate is higher than when the others match).

<<Sort>>

The extracting unit 102 lists claims (i.e., all claims of all patent documents) in order of a high matching rate or a low matching rate based on the calculated matching rate.

Further, the extracting unit 102 may be configured to list claims 1's (i.e., the claim having the broadest patent right) of each of the patent documents in order of a high matching rate or a low matching rate.

<<Output of Result>>

The extracting unit 102 transmits information of a certain claim (for example, a predetermined number of claims having a high matching rate order) among the listed claims to the user terminal 20. For example, the extracting unit 102 transmits information for identifying a claim, such as a patent number and a claim number, to the user terminal 20.

The extracting unit 102 may be configured to transmit information of a certain portion of claims 1's (for example, a predetermined number of claims 1's having a high matching rate order) among the listed claims 1's to the user terminal 20. For example, the extracting unit 102 transmits information (a patent number or the like) for identifying a patent document recited in claim 1 to the user terminal 20.

<Method>

Hereinafter, processing of <Extracting Product Relating to Patent>, <Extracting Patent Relating to Product>, and <Extracting Patent Relating to Formulation> will be described.

Figure 6:
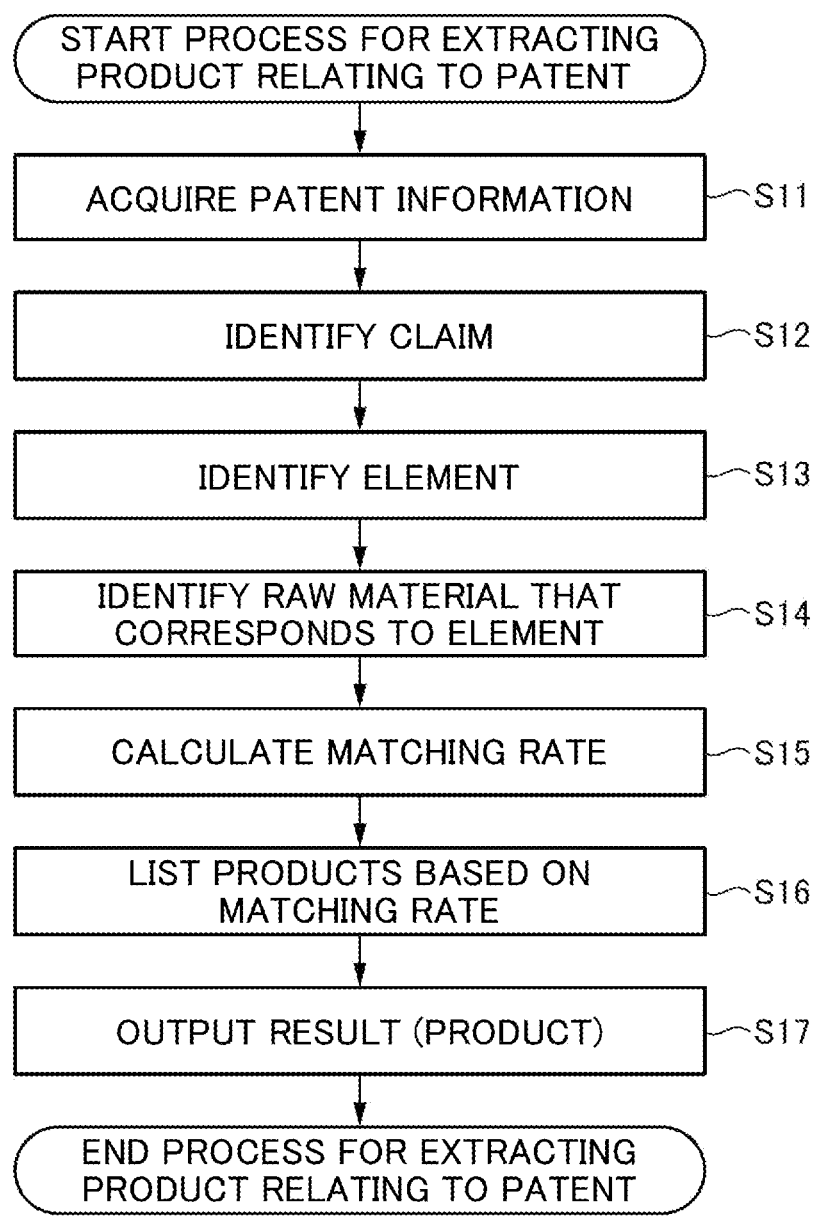
FIG. 6 is a flowchart of a process for extracting a product relating to a patent according to an embodiment of the present invention.

FIG. 6 is a flowchart of a process for extracting a product relating to a patent according to an embodiment of the present invention.

In step 11 (S11), the acquiring unit 101 acquires the patent information from the user terminal 20.

In step 12 (S12), the extracting unit 102 identifies a claim based on the patent information acquired in S11.

In step 13 (S13), the extracting unit 102 identifies all elements recited in the claim identified in in S12 with reference to the patent database 103.

In step 14 (S14), the extracting unit 102 identifies all raw materials that correspond to each of the elements identified in S13 with reference to the patent database 103.

In step 15 (S15), the extracting unit 102 calculates a matching rate between the raw material identified in S14 and the raw material contained in the product.

In step 16 (S16), the extracting unit 102 lists the products based on the matching rate calculated in S15.

In step 17 (S17), the extracting unit 102 transmits information of a certain product (for example, a predetermined number of products having a high matching rate order) among the products listed in S16 to the user terminal 20.

Figure 7:
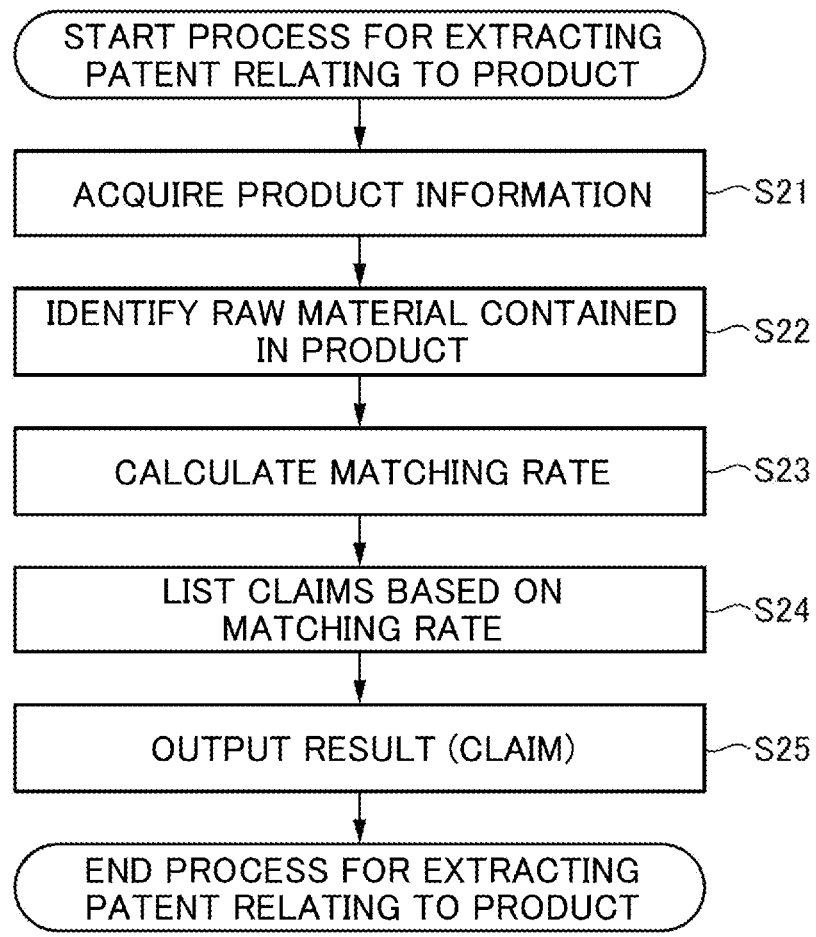
FIG. 7 is a flowchart of a process for extracting a patent relating to a product according to an embodiment of the present invention.

FIG. 7 is a flowchart of a process for extracting a patent relating to a product according to an embodiment of the present invention.

In step S21, the acquiring unit 101 acquires product information from the user terminal 20.

In step 22 (S22), the extracting unit 102 identifies the raw material contained in the product to be identified by the product information acquired in S21 with reference to the product database 104.

In step 23 (S23), the extracting unit 102 calculates a matching rate between the raw material identified in S22 and the raw material that corresponds to the element recited in the claim.

In step 24 (S24), the extracting unit 102 lists the claims (i.e., all claims of all patent documents) based on the matching rate calculated in S23.

In step 25 (S25), the extracting unit 102 transmits information of a certain claims listed in S24 (for example, a predetermined number of claims having a high matching rate order) to the user terminal 20.

Figure 8:
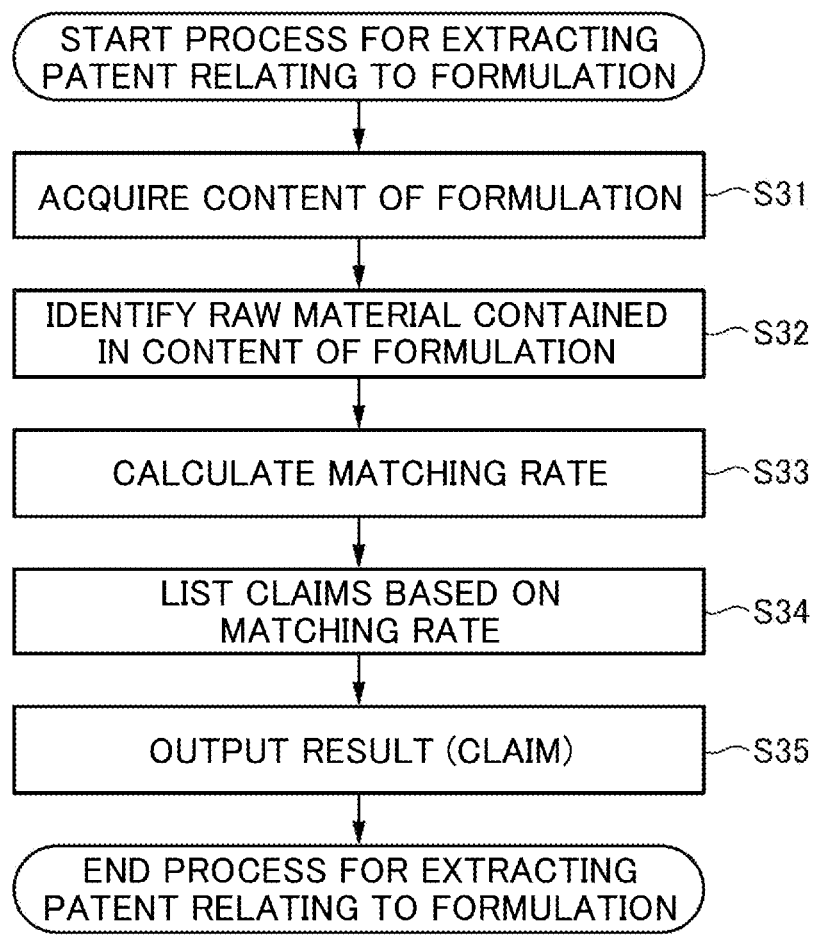
FIG. 8 is a flowchart of a process for extracting a patent relating to a formulation according to an embodiment of the present invention.

FIG. 8 is a flowchart of a process for extracting a patent relating to formulation according to an embodiment of the present invention.

In step (S31), the acquiring unit 101 acquires the formulation from the user terminal 20. The formulation includes information of the raw material required to make a product such as cosmetics.

In step 32 (S32), the extracting unit 102 identifies the raw material contained in the formulation acquired in S31.

In step 33 (S33), the extracting unit 102 calculates a matching rate between the raw material identified in S32 and the raw material that corresponds to the element recited in the claim.

In step 34 (S34), the extracting unit 102 lists the claims (i.e., all claims of all patent documents) based on the matching rate calculated in S33.

In step 35 (S35), the extracting unit 102 transmits information of certain claims listed in S34 (for example, a predetermined number of claims having a high matching rate order) to the user terminal 20.

<Effect>

As described above, in an embodiment of the present invention, a product that is likely within the technical scope of the patented invention can be easily extracted. Further, in an embodiment of the present invention, a patent that is likely to be infringed by the product can be easily extracted.

<Hardware Configuration>

Figure 9:
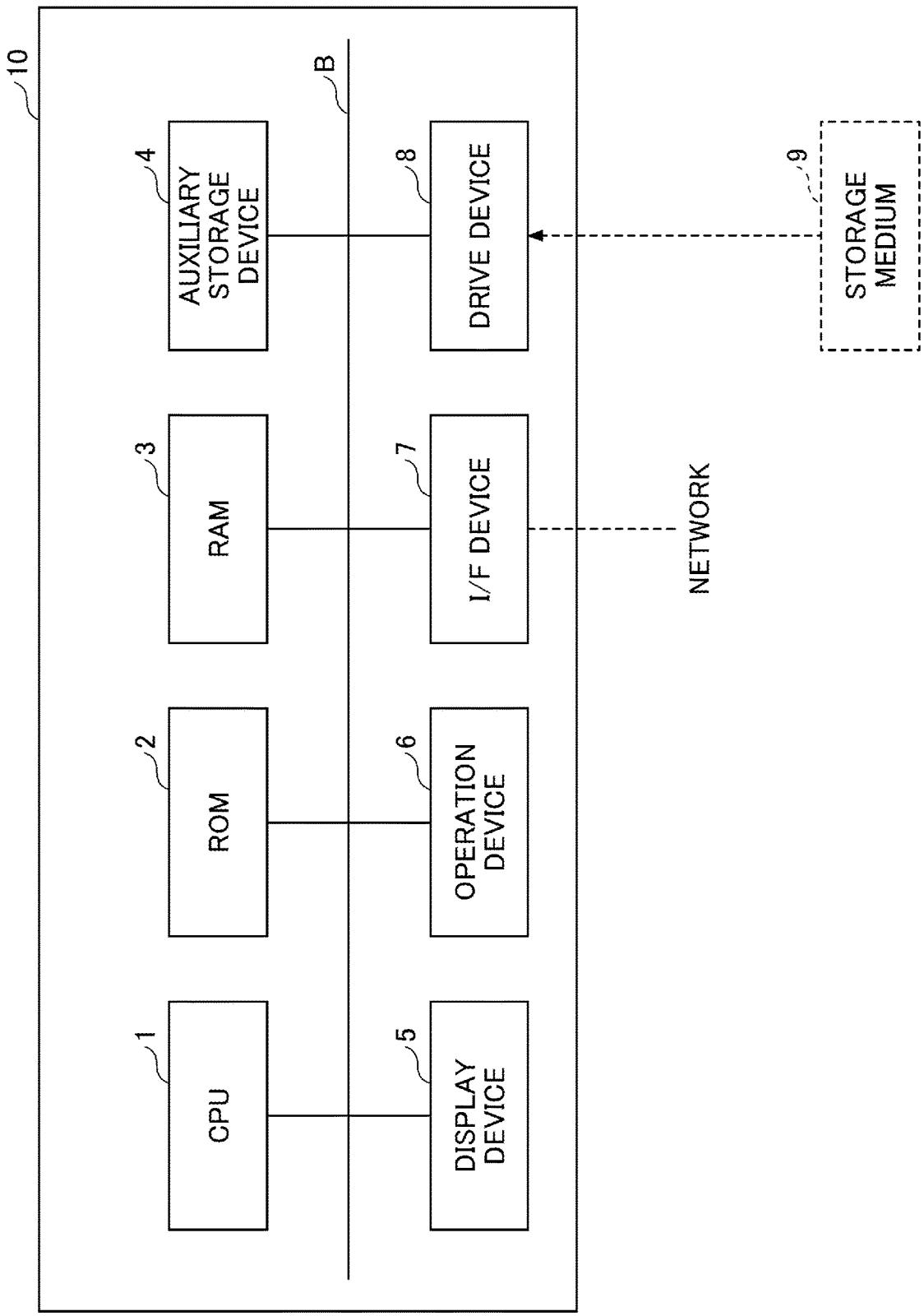
FIG. 9 is a block diagram illustrating an example of a hardware configuration of the information processing system according to an embodiment of the present invention.

FIG. 9 is a block diagram illustrating an example of a hardware configuration of the information processing system 10 according to an embodiment of the present invention. The information processing system 10 includes a Central Processing Unit (CPU) 1, a Read Only Memory (ROM) 2, and a Random Access Memory (RAM) 3. The CPU 1, the ROM 2, and the RAM 3 form a so-called computer.

The information processing system 10 may include an auxiliary storage device 4, a display device 5, an operation device 6, an I/F (interface) device 7, and a drive device 8. Each of the hardware of the information processing system 10 is connected to each other via the bus B.

The CPU 1 is an arithmetic unit that executes various programs installed in the auxiliary storage device 4.

The ROM 2 is a non-volatile memory. The ROM 2 functions as a main storage device that stores various programs and data necessary for executing various programs installed in the auxiliary storage device 4 by the CPU 1. Specifically, the ROM 2 functions as a main storage device that stores boot programs such as a Basic Input/Output System (BIOS) and an Extensible Firmware Interface (EFI).

The RAM 3 is a volatile memory such as a Dynamic Random Access Memory (DRAM) and a Static Random Access Memory (SRAM). The RAM 3 functions as a main storage device that provides a workspace deployed when various programs installed in the auxiliary storage device 4 are executed by the CPU 1.

The auxiliary storage device 4 is an auxiliary storage device that stores various programs or information to be used when the various programs are executed.

The display device 5 is a display device that displays an internal state or the like of the information processing system 10.

The operation device 6 is an input device in which an administrator of the information processing system 10 inputs various instructions to the information processing system 10.

The I/F device 7 is a communication device for connecting to a network and communicating with the user terminal 20.

The drive device 8 is a device for setting the storage medium 9. The storage medium 9 herein includes a medium for optically, electrically, or magnetically recording information, such as a CD-ROM, a flexible disk, or a magneto-optical disk. Further, the storage medium 9 may include a semiconductor memory or the like that electrically records information, such as an Erasable Programmable Read Only Memory (EPROM), a flash memory, or the like.

For example, various programs installed in the auxiliary storage device 4 are installed when the distributed storage medium 9 is set in the drive device 8 and various programs recorded in the storage medium 9 are read out by the drive device 8. Alternatively, various programs installed in the auxiliary storage device 4 may be installed by being downloaded from the network via the I/F device 7.

Although example embodiments have been described in detail above, the invention is not limited to the embodiments described above, and various modifications and substitutions can be made to the embodiments described above without departing from the scope of the claims.

This international application claims priority based on Japanese Patent Application No. 2019-197177 filed on Oct. 30, 2019, and the entire contents of Japanese Patent Application No. 2019-197177 are incorporated herein by reference.

DESCRIPTION OF SYMBOLS 10 information processing system
20 user terminal
30 network
101 acquiring unit
102 extracting unit
103 patent database
104 product database

The invention claimed is:

1. An information processing system comprising:
a memory storing a database in which a term associated with a raw material recited in a claim of a patent document and a raw material corresponding to the term are associated with each other; and
a processor configured to:
    acquire patent information; and
        extract a plurality of products each containing a raw material that corresponds to a term recited in a claim that is identified by the patent information, with reference to the database and a correspondence between a product and a raw material contained in the product, based on whether the raw material that corresponds to the term and the raw material contained in the product match, including calculating a matching rate between each of the products and the term recited in the claim, wherein the matching rate is calculated by weighting at least two of properties selected from: a raw material, a blending amount, an item classification, a container, an application destination, an emulsification form, a dosage form, a viscosity and pH, wherein the item classification indicates a category to which a substance belongs; and wherein the container contains (i) a substance related to the invention described in the claim, (ii) a product, or (iii) a substance produced by a formulation;

transmit information of the plurality of extracted products to a user terminal; and automatically move information of the products that have higher matching rate associated with the term to a position proximal to a top of a list displayed on the user terminal.

2. The information processing system according to claim 1, wherein the database and the correspondence further include information of at least one of the properties selected from: the item classification, the container, the target portion, the emulsified type, the dosage form, the viscosity, and the pH, and the processor further performs extraction based on whether information of at least one of the item classification, the container, the target portion, the emulsified type, the dosage form, the viscosity, and the pH with regard to the claim matches information of at least one of the item classification, the container, the target portion, the emulsified type, the dosage form, the viscosity, and the pH with regard to the product.

3. The information processing system according to claim 1, wherein the product is a cosmetic.

4. An information processing system comprising:

a memory storing a database in which a term associated with a raw material recited in a claim of a patent document and a raw material that corresponds to the term are associated with each other;

a processor configured to:

acquire a formulation, the formulation containing a raw material; and extract a plurality of claims reciting the term associated with the raw material contained in the acquired formulation, with reference to the database, based on whether the raw material contained in the formulation matches the raw material corresponding to the term, including calculating a matching rate between the term recited in the claims and the formulation, wherein the matching rate is calculated by weighting at least two of properties selected from: a raw material, a blending amount, an item classification, a container, an application destination, an emulsification form, a dosage form, a viscosity and pH, wherein the item classification indicates a category to which a substance belongs; and wherein the container contains (i) a substance related to the invention described in the claim, (ii) a product, or (iii) a substance produced by a formulation;

transmit information of the plurality of extracted claims to a user terminal; and automatically move the claims that have higher matching rate associated with the formulation to a position proximal to a top of a list displayed on the user terminal.

5. The information processing system according to claim 4, wherein the formulation is a cosmetic formulation.

6. An information processing system comprising:

a memory storing a database in which a term associated with a raw material recited in a claim of a patent document and a raw material corresponding to the term are associated with each other; and a processor configured to:

acquire product information for identifying a product; and extract a plurality of claims reciting the term associated with the raw material contained in the product that is identified by the acquired product information, with reference to the database and a correspondence between the product and the raw material contained in the product, based on whether the raw material contained in the product and the raw material that corresponds to the term match, including calculating a matching rate between the term recited in the claims and the product, wherein the matching rate is calculated by weighting at least two of properties selected from: a raw material, a blending amount, an item classification, a container, an application destination, an emulsification form, a dosage form, a viscosity and pH, wherein the item classification indicates a category to which a substance belongs; and wherein the container contains (i) a substance related to the invention described in the claim, (ii) a product, or (iii) a substance produced by a formulation;

transmit information of the plurality of extracted claims to a user terminal; and automatically move the claims that have higher matching rate associated with the product to a position proximal to a top of a list displayed on the user terminal.

7. The information processing system according to claim 1, wherein the raw material is identified by at least one of an International Nomenclature of Cosmetic Ingredients (INCI) name, a Monograph ID (MID), or a Chemical Abstracts Service (CAS) registry number (registered trademark).

8. The information processing system according to claim 4, wherein the database and the formulation further includes information of at least one of the properties selected from: the item classification, the container, the target portion, the emulsified type, the dosage form, the viscosity, and the pH, and the processor further performs extraction based on whether information of at least one of the item classification, the container, the target portion, the emulsified type, the dosage form, the viscosity, or the pH with regard to the formulation matches information of at least one of the item classification, the container, the target portion, the emulsified type, the dosage form, the viscosity, and the pH with regard to the claim.

9. A method implemented by an information processing system, the method comprising:

acquiring patent information, product information, or a formulation, the formulation containing a raw material; and (a) extracting a plurality of products each containing a raw material that corresponds to a term recited in a claim that is identified by the patent information, with reference to a database in which a term associated with a raw material recited in a claim of a patent document and a raw material that corresponds to the term are associated with each other and a correspondence between a product and a raw material contained in the product, based on whether the raw material that corresponds to the term and the raw material contained in the product match, including calculating a matching rate between each of the products and the term recited in the claim, wherein the matching rate is calculated by weighting at least two of properties selected from: a raw material, a blending amount, an item classification, a container, an application destination, an emulsification form, a dosage form, a viscosity and pH, wherein the item classification indicates a category to which a substance belongs; and wherein the container contains (i) a substance related to the invention described in the claim, (ii) a product, or (iii) a substance produced by a formulation;

transmitting information of the plurality of extracted products to a user terminal; and automatically moving information of the products that have higher matching rate associated with the term to a position proximal to a top of a list displayed on the user terminal;

(b) extracting a plurality of claims reciting the term associated with the raw material contained in a product that is identified by the acquired product information, with reference to the database and the correspondence between the product and the raw material contained in the product, based on whether the raw material contained in the product and the raw material that corresponds to the term match, including calculating a matching rate between the term recited in the claims and the product, wherein the matching rate is calculated by weighting at least two of properties selected from: a raw material an element, a blending amount, an item classification, a container, an application destination, an emulsification form, a dosage form, a viscosity and pH, wherein the item classification indicates a category to which a substance belongs; and wherein the container contains (i) a substance related to the invention described in the claim, (ii) a product, or (iii) a substance produced by a formulation;

transmitting information of the plurality of extracted claims to a user terminal; and automatically moving the claims that have higher matching rate associated with the product to a position proximal to a top of a list displayed on the user terminal; or (c) extracting a plurality of claims reciting the term associated with the raw material contained in the acquired formulation, with reference to the database, based on whether the raw material contained in the formulation and the raw material that corresponds to the term match, including calculating a matching rate between the term recited in the claims and the formulation, wherein the matching rate is calculated by weighting at least two of properties selected from: a raw material, a blending amount, an item classification, a container, an application destination, an emulsification form, a dosage form, a viscosity and pH, wherein the item classification indicates a category to which a substance belongs; and wherein the container contains (i) a substance related to the invention described in the claim, (ii) a product, or (iii) a substance produced by a formulation;

transmitting information of the plurality of extracted claims to a user terminal; and automatically moving the claims that have higher matching rate associated with the formulation to a position proximal to a top of a list displayed on the user terminal.

10. The information processing system according to claim 6, wherein the processor extracts a claim that recites all or part of terms associated with the raw material contained in the product.

11. A non-transitory computer-readable recording medium having stored therein a program that causes a processor of an information processing system to function as:

acquire patent information, product information, or a formulation, the formulation containing a raw material; and (a) extract a plurality of products each containing a raw material that corresponds to a term recited in a claim that is identified by the patent information, with reference to a database in which a term associated with a raw material recited in a claim of a patent document and a raw material that corresponds to the term are associated with each other and a correspondence between a product and a raw material contained in the product, based on whether the raw material that corresponds to the term and the raw material contained in the product match, including calculating a matching rate between each of the products and the term recited in the claim, wherein the matching rate is calculated by weighting at least two of properties selected from: a raw material, a blending amount, an item classification, a container, an application destination, an emulsification form, a dosage form, a viscosity and pH, wherein the item classification indicates a category to which a substance belongs; and wherein the container contains (i) a substance related to the invention described in the claim, (ii) a product, or (iii) a substance produced by a formulation;

transmit information of the plurality of extracted products to a user terminal; and automatically move information of the products that have higher matching rate associated with the term to a position proximal to a top of a list displayed on the user terminal;

(b) extract a plurality of claims reciting the term associated with the raw material contained in a product that is identified by the acquired product information, with reference to the database and the correspondence between the product and the raw material contained in the product and extract, based on whether the raw material contained in the product and the raw material that corresponds to the term match, including calculating a matching rate between the term recited in the claims and the product, wherein the matching rate is calculated by weighting at least two of properties selected from: a raw material, a blending amount, an item classification, a container, an application destination, an emulsification form, a dosage form, a viscosity and pH, wherein the item classification indicates a category to which a substance belongs; and wherein the container contains (i) a substance related to the invention described in the claim, (ii) a product, or (iii) a substance produced by a formulation;

transmit information of the plurality of extracted claims to a user terminal; and automatically move the claims that have higher matching rate associated with the product to a position proximal to a top of a list displayed on the user terminal; or (c) extract a plurality of claims reciting the term associated with the raw material contained in the acquired formulation, with reference to the database, based on whether the raw material contained in the formulation and the raw material that corresponds to the term match, including calculating a matching rate between the term recited in the claims and the formulation, wherein the matching rate is calculated by weighting at least two of properties selected from: a raw material, a blending amount, an item classification, a container, an application destination, an emulsification form, a dosage form, a viscosity and pH, wherein the item classification indicates a category to which a substance belongs; and wherein the container contains (i) a substance related to the invention described in the claim, (ii) a product, or (iii) a substance produced by a formulation;

transmit information of the plurality of extracted claims to a user terminal; and automatically move the claims that have higher matching rate associated with the formulation to a position proximal to a top of a list displayed on the user terminal.

12. The information processing system according to claim 4, wherein the processor extracts a claim that recites all or part of terms associated with the raw material contained in the formulation.

13. A non-transitory computer-readable recording medium having stored therein a data structure in which a term associated with a raw material recited in a claim of a patent document and a raw material that corresponds to the term are associated with each other, wherein an information processing system acquires patent information, product information, or a formulation, the formulation containing a raw material, and wherein the data structure is used to
extract a plurality of products each containing the raw material that corresponds to the term recited in the claim that is identified by the acquired patent information;

or the data structure is used to extract a plurality of claims reciting the term associated with the raw material contained in the product that is identified by the acquired product information or the raw material contained in the acquired formulation; and (a) transmit information of the plurality of extracted products and automatically move information of the products that have higher matching rate associated with the term recited in the claim to a position proximal to a top of a list displayed on the user terminal, wherein the matching rate is calculated by weighting at least two of properties selected from: a raw material, a blending amount, an item classification, a container, an application destination, an emulsification form, a dosage form, a viscosity and pH, wherein the item classification indicates a category to which a substance belongs; and wherein the container contains (i) a substance related to the invention described in the claim, (ii) a product, or (iii) a substance produced by a formulation, or (b) transmit information of the plurality of extracted claims to a user terminal and automatically move the claims that have higher matching rate associated with the raw material contained in the product that is identified by the acquired product information or the raw material contained in the acquired formulation to a top of a list displayed on the user terminal, wherein the matching rate is calculated by weighting at least two of properties selected from: a raw material, a blending amount, an item classification, a container, an application destination, an emulsification form, a dosage form, a viscosity and pH, wherein the item classification indicates a category to which a substance belongs; and wherein the container contains (i) a substance related to the invention described in the claim, (ii) a product, or (iii) a substance produced by a formulation.

14. The information processing system according to claim 1, wherein the item classification refers to a category to which (i) a substance of an invention described in a claim, (ii) a product, or (iii) a substance produced by a formulation, belongs.

15. The information processing system according to claim 1, wherein the item classification refers to (i) a category for classifying a substance related to the invention described in the claim according to the substance's intended use, (ii) a category for classifying a product according to the product's intended use, or (iii) a category for classifying a substance made by a formulation according to the substance's intended use.

16. The information processing system according to claim 1, wherein the database and the correspondence further includes a blending amount of the raw material, and the processor further performs extraction based on whether the blending amount of the raw material that corresponds to the term matches the blending amount of the raw material contained in the product.

17. The information processing system according to claim 4, wherein the database and the formulation further includes a blending amount of the raw material, and the processor further performs extraction based on whether the blending amount of the raw material contained in the formulation matches the blending amount of the raw material that corresponds to the term.

* * * * *